United States Patent [19]

Lemonnier

[11] Patent Number: 4,777,137

[45] Date of Patent: Oct. 11, 1988

[54] METHOD AND APPARATUS FOR MICROBIOLOGICAL TESTING OF LIQUIDS

[75] Inventor: Jean Lemonnier, Le Vesinet, France

[73] Assignee: Millipore Corporation, Bedford, Mass.

[21] Appl. No.: 691,687

[22] Filed: Jan. 15, 1985

[30] Foreign Application Priority Data

Jan. 31, 1984 [FR] France .................................. 84 01470

[51] Int. Cl.$^4$ ......................... C12M 1/16; C12M 1/12; C12M 1/26; C12Q 1/04

[52] U.S. Cl. ..................... 435/299; 435/311; 435/292; 435/34; 210/244; 210/476; 210/477; 210/321.84

[58] Field of Search ................... 435/30, 31, 311, 292, 435/293, 34, 294, 299; 422/101; 206/45.31, 218, 569; 210/493.1, 350, 476, 482, 477, 499, 416.1, 405, 244, 321.84

[56] References Cited

U.S. PATENT DOCUMENTS

| | | | |
|---|---|---|---|
| 973,723 | 10/1910 | Thomson | 210/476 |
| 2,923,669 | 2/1960 | Poitras | 435/30 X |
| 3,682,596 | 8/1972 | Stone | 422/101 |
| 3,929,583 | 12/1975 | Sharpe et al. | 435/311 X |
| 4,025,306 | 5/1977 | Studer | 435/30 X |
| 4,036,698 | 7/1977 | Bush et al. | 435/31 |
| 4,062,773 | 12/1977 | Leonard | 210/493.1 X |
| 4,292,405 | 9/1981 | Mascoli et al. | 435/31 |
| 4,351,900 | 9/1982 | Lemonnier | 435/30 X |
| 4,441,996 | 4/1984 | Hurst | 210/244 X |
| 4,526,752 | 7/1985 | Perlman et al. | 422/56 |
| 4,650,662 | 3/1987 | Goldfinger et al. | 422/102 X |

Primary Examiner—Robert J. Warden
Assistant Examiner—Randall E. Deck
Attorney, Agent, or Firm—Andrew T. Karnakis; Paul J. Cook

[57] ABSTRACT

Method and apparatus for the microbiological testing of liquids to identify and count living microorganisms contained therein includes a tubular sleeve for collecting the liquid sample to which there is attached at one end a microporous membrane filter. Each end of the sleeve has the shape of a female receptacle portion where into one end a container housing a culture medium can be nested by force for applying the medium to the underside of the filter and where into the other end a cover can be nested to provide a substantially tight sealing of the device. Preferably, the tubular sleeve is in the form of a bellows the convolutions of which can be either compressed or expanded to correspondingly alter the volume of the sleeve between minimum and maximum values.

5 Claims, 13 Drawing Sheets

METHOD AND APPARATUS FOR MICROBIOLOGICAL TESTING OF LIQUIDS

FIELD OF THE INVENTION

This invention relates to a device and a process for the microbiological testing of liquids to permit identification and counting of living microorganisms contained in a sample of the liquid to be analyzed.

BACKGROUND OF THE INVENTION

In many industries, particularly the alimentary, pharmaceutical and electronic industries, as well as in hospitals, it is essential to be able to evaluate the degree of contamination of a number of liquids by microorganisms, i.e., bacteria, yeasts or molds.

To effect such an evaluation, it is preferable to use membrane filtration techniques as opposed to the process of growing a culture medium in a Petri dish which only permits analysis of samples of a small volume.

The membrane filtration method consists of filtering the sample through a sterile membrane placed on a porous holder onto which a funnel for receiving the sample is sealingly fixed. Prior to filtration, both the holder and the funnel are decontaminated.

After filtration, which is generally effected through a vacuum flask, and rinsing to eliminate bacteriostatic agents possibly present, the membrane is removed with sterile forceps and deposited onto a gelatinous culture medium contained in a Petri dish. The Petri dish is then incubated at a suitable temperature for the time necessary for the microorganisms to be able to develop and multiply sufficiently to form colonies visible to the naked eye to permit them to be identified and counted.

This known membrane filtration method permits evaluation of even slightly contaminated samples because the microorganisms are concentrated on the membrane, and it is possible to filter a significant volume of sample to collect a sufficient number of microorganisms. However, this method presents certain disadvantages. First, it must be carried out in a major laboratory involving many sterilized utensils and the use of specialized personnel because of the complicated manipulations required. Also the rinsing of the membrane by a sterile rinsing liquid does not always reach the peripheral zones where the membrane is clamped between its holder and the funnel bottom. Thus any bacteriostatic agents possibly present may be retained in such zones and may migrate upon incubation thereby hampering multiplication of the microorganisms to be counted.

Moreover, care must be exercised in placing the membrane filter upon the culture medium in the Petri dish to avoid entrapping any air bubbles between the culture medium and the membrane which would prevent contact between the culture medium and a portion of the surface of the membrane thereby opposing diffusion of the culture medium, and inhibiting microorganism development.

Finally, the use of vacuum filtration does not allow verification that the filter membrane, the pore diameter of which was calculated to retain a certain type of microorganism (e.g., 0.45 micrometers for bacteria) remained intact during the manipulations to which it was submitted.

To remedy some of these inconveniences, a filtration procedure has been proposed consisting of using a sterile box with circular elements nested into one another and a removable cover. This box includes an inlet and an outlet disposed on both sides of a holder on which an absorbent pad and a filtration membrane lie, clamped at the periphery to the holder by one of the circular elements. After filtration, which is generally accomplished through aspiration of the sample that passes successively through the membrane and then the absorbent pad, a culture medium is introduced through the outlet, that is, counter-currently to normal operation, to saturate the absorbent pad. Once the outlet has been obstructed, the box can be directly brought to the incubator to permit the collected microorganisms to develop.

Although this membrane filtration method using a sterile box avoids membrane manipulation by an operator, and permits the samples to be directly taken on the site, it has, however, serious drawbacks. First, the membrane diameter increases when it becomes wetted and since the membrane and the absorbent pad, which are clamped at their periphery to the sterile box are kept dry prior to use, upon filtration of the sample the wetting of the pad and membrane may cause the membrane filter to part from the absorbent pad. This prevents contact between the membrane and the pad saturated with the culture medium, and thus disturbs development of the microorganism colonies upon incubation.

In the same manner as in the preceding techniques, it is not possible to prevent, in spite of membrane rinsing, migration of bacteriostatic agents retained in the peripheral zone of the membrane to its center where these agents could inhibit development of the microorganisms to be counted. Similarly, as the absorbent pad which is wetted upon filtration of the sample can also contain growth inhibiting elements, the culture medium with which the absorbent pad is subsequently saturated can become proportionately diluted and possibly modified by such elements. Finally, introduction of the culture medium in a counter-current direction on the absorbent pad may cause the membrane to be lifted and moved away from the pad thereby forcibly causing disturbance in the growth of the microorganisms to be counted.

A third filtration method consists of using a sampler of the "dipstick" type which as indicated by its name is in form of a dipstick and comprises a membrane filter covering an absorbent pad impregnated with a culture medium dried by lyophilization. By dipping this sampler into the liquid to be analyzed, there is pumped by capillary action through the membrane a certain volume of liquid which saturates the lyophilized culture medium by solubilizing it. The impregnated dipstick can be directly brought to incubation.

This third filtration procedure is however of a limited use since it can hardly ever be used for analyzing water. The analyzed sample volume is in the order of a few cubic centimeters ($cm^3$) only and the reconstitution of a culture medium involves supplementary risks as compared to the techniques discussed above.

SUMMARY OF THE INVENTION

This invention consists of a device and process for membrane filtration of liquid samples to conduct microbiological testing that avoids the above mentioned drawbacks.

In accordance with a preferred embodiment, the device according to the invention is characterized by a sleeve, in particular, a tubular sleeve, the bottom of which is closed by a microporous membrane filter sealingly fixed on its periphery to one end of the sleeve. Each end of the sleeve has the shape of a female receptacle portion where into one of said ends a container housing a culture medium can be nested by force for applying the medium under the membrane filter, whereas the other end can receive a cover for providing substantially tight sealing of the device.

Preferably, the tubular sleeve is in the form of a bellows the convolutions of which can be compressed or expanded to permit the sleeve to exhibit a minimum inner volume when the bellows is compressed and a maximum inner volume when the bellows is expanded. The female receptacle ends of the sleeve, whether the sleeve takes the form of a bellows or not, may each be formed with a substantially cylindrical portion for receiving the container and cover respectively.

In such a device, if, after filtration, the inner volume of the sleeve is slightly compressed by pushing the cover into the end remote from the membrane filter, the filter tends to bulge thereby permitting a filter integrity check on the one hand, and on the other hand, ensuring contact of the membrane filter with the culture medium contained in the container from the center to the periphery of the filter, thereby preventing entrapment of any air bubbles. When the container is forcibly nested into the filter end of the sleeve, tension is produced in the filter which eliminates undesirable folds in the membrane and permits contact of the entire membrane surface with the culture medium.

The device according to this invention is preferably intended for single usage and can be made ready for use in a particle-free, sterile and non-pyrogenic manner so as to collect a filtration sample of a volume corresponding to the maximum volume of the sleeve. However, when the sleeve takes the form of a bellows, the device may be packaged with the sleeve being compressed to minimize packing density, while, in operation, the device permits collection of a filtration sample of a relatively large volume corresponding to the inner volume of the expanded sleeve.

Moreover, when using a bellows configuration, filtration may occur selectively either in the laboratory by producing vacuum downstream of the membrane without the need for a vented filter since the sleeve may retract directly, or in the field by creating pressure upstream of the membrane by manual compression of the expanded sleeve containing the sample to be tested, i.e., by using the device as a pump.

This invention also relates to a process for microbiological testing of a liquid sample by means of a membrane filter which comprises the successive steps of introducing the sample to be tested into a sleeve, particularly a tubular sleeve, which may or may not take the form of a bellows, said sleeve being provided at its lower end with a membrane filter sealingly fixed at its periphery to the walls of the sleeve, filtering the sample through the membrane, and pressurizing the sleeve on the upstream side of the membrane to give the latter a bulging shape to facilitate contacting the downstream side of the membrane with a culture medium.

This process is intended for collecting samples of the liquid to be analyzed, the volume of which corresponds to that of the sleeve and can be several times that of the compressed sleeve when a bellows-shape sleeve is used; directly filtering the sample under field conditions where the sample was collected by collapsing the sleeve or compressing the sleeve of a bellows-configured device; checking the integrity of the membrane after filtration; and contacting the membrane with a culture medium under conditions suitable for avoiding entrapping any air bubbles, regardless of whether the sleeve is formed as a bellows or not.

Such a filtration process allows one to obtain a filtrate which can be either merely purified or sterilized, depending on the pore diameter and other characteristics of the membrane, thereby permitting the operator to use the filtrate, if need be, as a rinsing liquid.

DESCRIPTION OF THE DRAWINGS

This invention will now be described in reference to the attached drawings in which.

DESCRIPTION OF THE PREFERRED EMBODIMENTS

The device 1 according to this invention as shown in FIGS. 1 to 5 comprises either a straight sleeve 2A or a bellows-shaped sleeve 2B of a known structure, for example, such as described in French Pat. No. 2,467,146. The sleeves are provided with two ends 3, 4 in the form of female receptacles, and a membrane filter 5 is secured as as by welding to the periphery of the sleeve and serves as the sleeve bottom.

Figure 1:
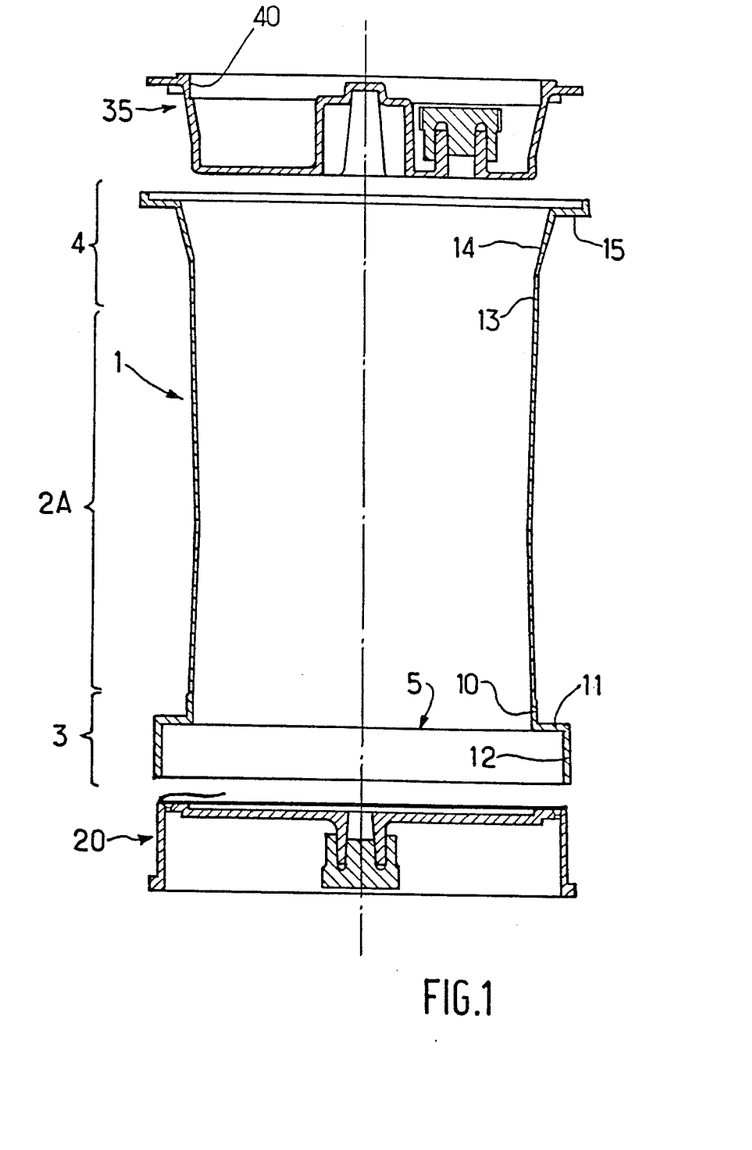
FIG. 1 is a front view in cross-section of a device according to a first embodiment of the invention having a non-bellows sleeve.
Figure 2:
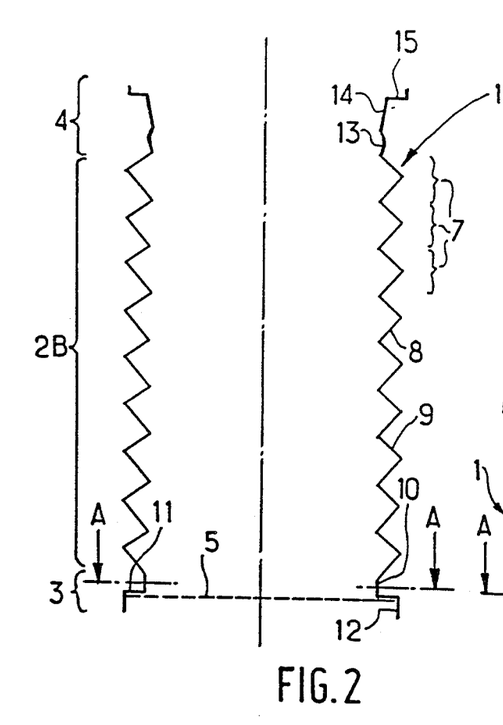
FIG. 2 is a front view in cross-section of a device according to a second embodiment of the invention having a bellows sleeve shown in its expanded position.
Figure 3:
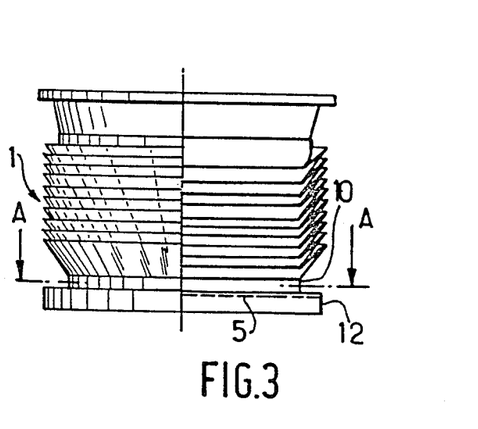
FIG. 3 is a view of the same device as in FIG. 2 showing the sleeve in a compressed position.
Figure 4:
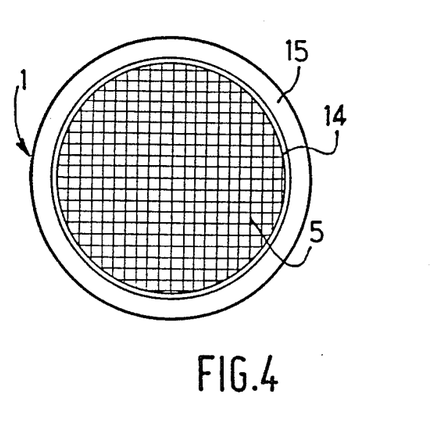
FIG. 4 is a top view of the device shown in FIGS. 2 and 3.

The sleeve 2A or 2B is of a generally cylindrical shape (see FIGS. 1 and 2) and when formed as a bellows consists of a series of convolutions 7 that may be expanded as shown in FIG. 2 or compressed as shown in FIG. 3 for providing the sleeve with an inner volume that varies in significant proportions, for example, from 1 to 5 times. Thus the device functions as a variable volume container the bottom of which is sealed by the membrane 5. Each of the convolutions 7 of the sleeve 2B may be of triangular cross-section defined by two unequal sides 8 and 9, each making a different acute angle with the longitudinal axis of the sleeve, the larger side 8 of the convolution preferably being connected to the end 3 of the sleeve where the membrane filter is located. Such a structure in which each convolution is asymmertric enables the sleeve to be stable when the bellows is compressed.

Figure 5:
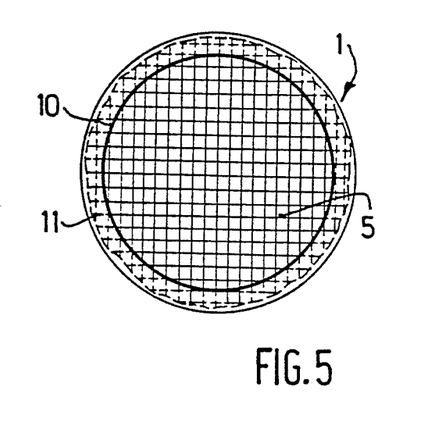
FIG. 5 is a sectional view along line A—A of FIGS. 2 and 3.

The ends 3, 4 forming the female receptacle of the sleeve 2A or 2B are integrally made with the sleeve but it is also possible to form these ends as a separate assembly. The end 3 located on the lower side of the sleeve where the membrane lies and shown in detail in FIGS. 1 and 2 includes a first substantially cylindrical portion 10 for connecting to the sleeve at the larger side 8 of the lowest convolution of the sleeve 2B, a circular edge portion 11 extending radially outwardly from the cylindrical portion 10 in a plane perpendicular to the sleeve axis, and a second substantially cylindrical portion 12. A membrane filter of a diameter approximately equal to that of the internal surface of the second cylindrical portion 12 is fixed to a peripheral crown at the lower face of the circular edge portion 11 as shown by FIGS. 1, 2 and 5.

The end 4 of the sleeve 2A or 2B remote from where the membrane lies also includes a substantially cylindrical portion 13 for connecting to the sleeve at the smaller side 9 of the highest convolution of the sleeve 2B, a conical connecting portion 14 flared outwardly from the portion 13, and a collar 15 extending radially outwardly in a plane substantially perpendicular to the sleeve axis from the connecting portion 14.

The device 1 shown in FIGS. 1 to 5 is generally made of a plastic material, preferably supple such as polyethylene, and is manufactured according to rigorous specifications with respect to the connection angle of the cylindrical portion 10 to the circular edge portion 11. It is recommended that this angle be a sharp angle so that the subsequent fixation of the membrane filter 5 to the lower face of the edge portion 11, as for example, by thermal welding, can be effected without the production of burrs or recesses therein that might retain bacteriostatic agents harmful to the development of the microorganisms to be collected on the membrane.

Figure 6:
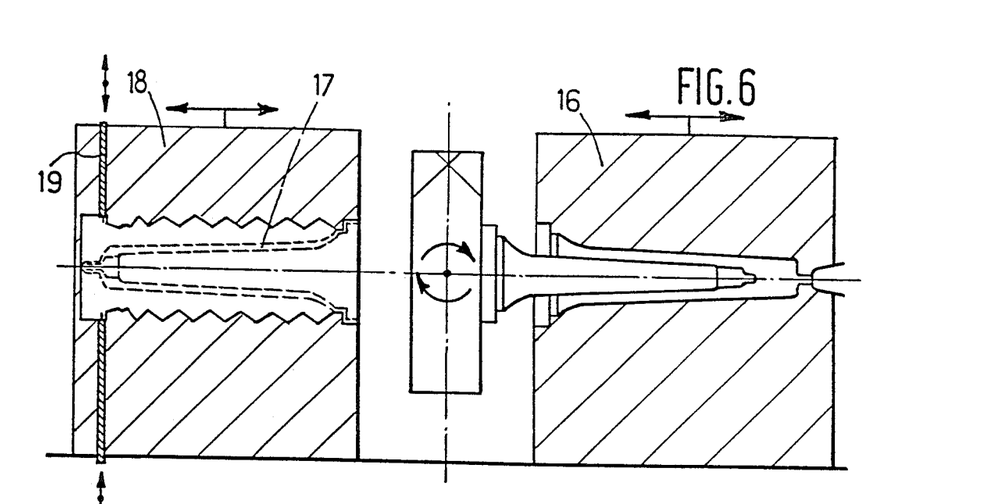
FIG. 6 is a schematic representation, in sectional view, of a machine for manufacturing the device of FIGS. 2, 3 and 4.

In order to satisfy these technical requirements when producing a device with the bellows sleeve 2B, the one-piece assembly consisting of the sleeve and both ends is manufactured through a welding process by injection blowing of plastic material during which first a preform is blown to produce the bellows-shaped sleeve 2B and the other end 4 of the device. This process can be carried out by means of the machine shown schematically in FIG. 6 wherein the plastic material is first injected into a mold 16 to obtain a preform 17 to the accurate dimensions of the end 3 to which the membrane 5 is subsequently secured. Then the preform 17 is blown into a mold 18 where the bellows sleeve 2B and the other end 4 are formed, the latter being severed by a knife 19. After the one piece assembly is prepared by injection blowing, the membrane filter is secured thereto, as for example by welding. Thus the filter is the only part added in order to obtain a completed device according to this invention.

The membrane filter 5 is of known type and is generally made of a plastic material of the cellulose ester type and has a pore diameter which varies depending on the size of the microorganisms to be retained. For bacteria the generally used pore diameter is 0.45 micrometers. Other hydrophilous or hydrophobic materials can be used for retention of other microorganisms. It should be noted that the membranes of any pore diameters are not impervious to gas when they are dry but become an impervious gas barrier when they are wetted up to a pressure called the bubble point. The surface of the membrane upon which microorganisms are collected includes preferably squared grid marking, and, if possible, each square is identified by indices to facilitate the counting of microorganism colonies which develop after incubation (see FIGS. 4, 5 and 28).

Figures 7, 8, 9, 10, 11:
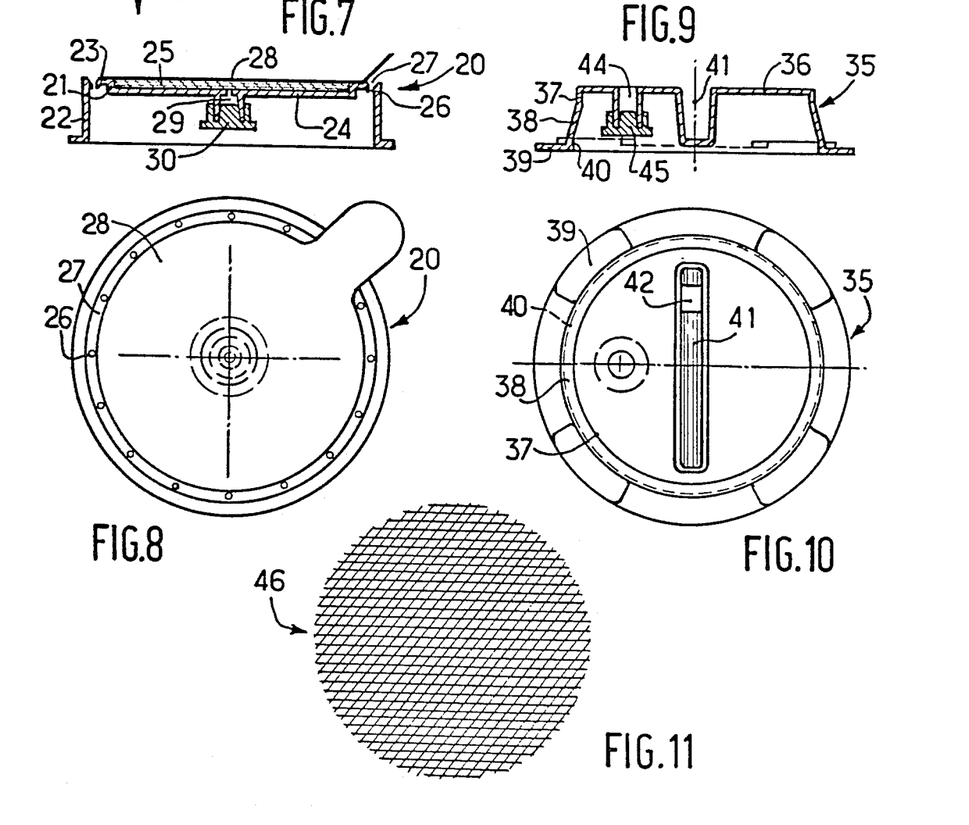
FIG. 7 is a front sectional view of a container according to the invention for receiving a culture medium and which is adapted to nest into the end adjacent the fixed membrane of either a bellows or non-bellows sleeve.
FIG. 8 is a top view of the container of FIG. 7.
FIG. 9 represents a front sectional view of the cover according to the invention for substantially sealingly closing that end of the sleeve (bellows or non-bellows configuration) remote from the end to which the membrane is fixed.
FIG. 10 is a top view of the cover of FIG. 9.
FIG. 11 is a top view of a circular spacer.

The container 20 which is used for receiving a culture medium is generally cylindrical and is adapted to be nested by force into the lower end 3 of the device 1 so as to apply the culture medium under the membrane filter 5. With reference more particularly to FIGS. 7 and 8, the container 20 consists of two substantially cylindrical and concentric elements 21 and 22 joined through a planar circular connecting crown or peripheral wall 23 perpendicular to the axis of the container. The outer face of the element 22 is preferably formed with a slight conicity for reasons to be explained hereinafter, while the inner element 21 includes a bottom surface 24 so as to define a hollow portion 25 for receiving a culture medium. The crown or peripheral wall 23 is provided with a number of axial holes 26 formed preferably in a circular groove 27 located on the upper face of the crown 23 (see FIG. 7). These holes are intended to be used as vents by providing a communications path from the space above the container to the space under the container and within the outer substantially cylindric element 22.

Figure 20:
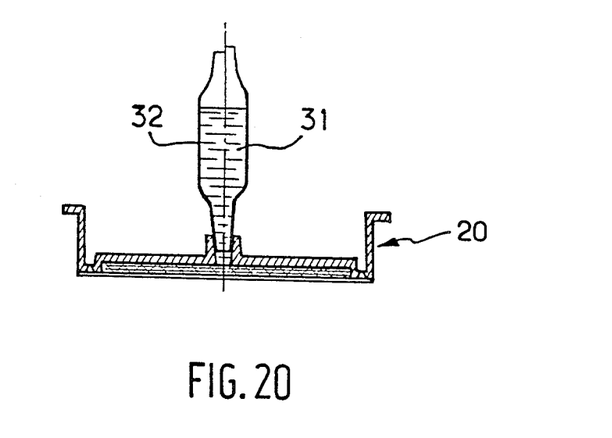
FIGS. 20 and 21 are sectional views of a container according to the invention showing the filling thereof with a culture medium.
Figure 21:
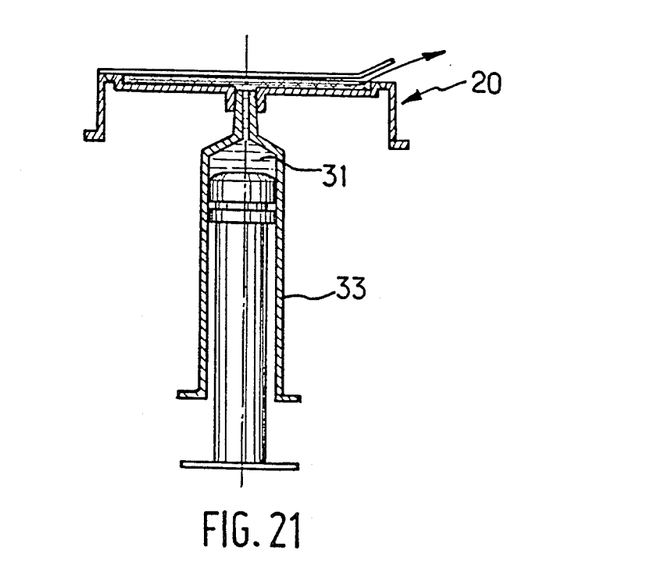

The hollow portion 25 is sealed by a removable sealing element 28 which may take the form of a filter or film located on at least a portion of the crown or peripheral wall 23 in such way as either not to cover the holes 26 (see FIGS. 7 and 8) or to cover said holes to ensure perfect tightness and sealing (see FIGS. 20 and 21).

In the embodiment of FIGS. 7 and 8, the hollow portion 25 contains an absorbent pad and the bottom surface 24 is formed with an axial opening 29 closed by a removable stopper 30. The opening is used for introduction of a liquid culture medium 31 which saturates the absorbent pad either through gravity from a flask 32 or by pressure by means of a plastic flask or syringe 33 as represented in FIGS. 20 and 21 respectively. It may be desirable to partially remove the sealing element 28 to discharge pressure from the hollow portion. In the embodiment shown in FIG. 24, the hollow portion 25 was directly filled with a gelatanious culture medium 34. The corresponding container 20 is ready for use (preferably a single use) and is adapted to be commercialized as a prefilled unit.

The container 20 is made of a plastic material, preferably rigid plastic such as polystyrene, for being nested by force into the end 3 of the sleeve 2A or 2B which is made of preferably supple polyethylene. Thus there is a tendency to produce a radial tension directed outwardly toward said sleeve end when the container is so nested, and particularly so when the element 22 has a slight conicity.

The cover 35 is also made of plastic and is preferably only used once according to the invention, and provides a practically tight sealing of the device 1 at the end 4 remote from where the membrane filter 5 is welded. In the embodiment shown in detail in FIGS. 9 and 10, the cover 35 comprises a circular bottom 36 the edges of which connect to a cylindrical portion 37 which preferably flares outwardly into a conical portion 38 to terminate in a collar 39 extending radially outwardly in a plane substantially perpendicular to the axis of the cover. The dimensions of the cylindrical and conical portions of the cover are so determined as to allow a tight fit of the cover into the substantially cylindrical portion 13 and conical portion 14 portion of the end 4 of the device 1.

Figure 28:
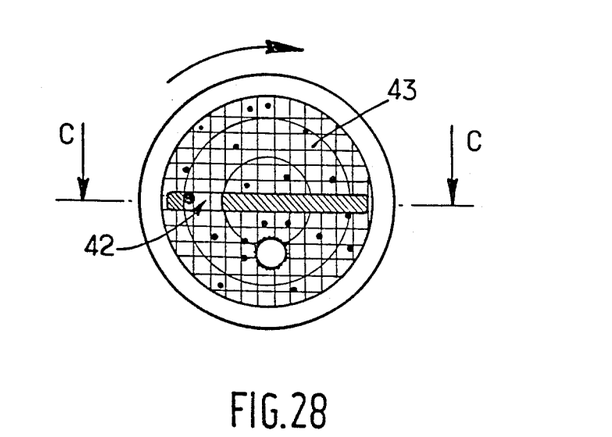
FIGS. 28 and 29 are respective top and sectional views taken along line CC of FIG. 28 of the device according to the invention in a position for counting the microorganisms.

The inner circular edge of the collar 39 presents a small inner cylindrical portion 40 the diameter of which corresponds to the outer diameter of the cylindrical portion 10 of the end 3 so as to be nestable therein. The circular bottom 36 of the cover includes a hollow portion 41 which in the illustrated case extends symmetrically on either side of the cover axis along the majority of the diameter thereof except at the end so as not to prevent the cover from tightly contacting the inner walls of the end 4 formed as the female receptacle. The bottom of the hollow portion 41 can have a convex curve as in a magnifying glass and extends to a depth within a few millimeters of the plane formed by the collar 39. This hollow portion is preferably opaque except for a transparent observation window 42 which functions as a magnifying glass of a generally rectangular cross-section as shown in FIG. 28 such that as the cover rotates an observation zone 43 is generated that corresponds to a percentage (e.g., 50%) of the total surface area of the membrane filter 5. In the case of a bellows sleeve 2B device, all or part of the cover may form a magnifying glass the magnification of which can be adjusted by extending or retracting the sleeve. The cover bottom may also be formed with one or several openings 44, for example midway between the axis and the periphery of the cover with each opening being closed by a removable closure 45. The cover 35 is preferably made of rigid polystyrene. The intermediary conical portion 38 between the cylindrical portion 37 and the collar 39 may be dispensed with as may the conical portion 14 of the sleeve.

The device according to the invention can also include a circular spacer 46 the diameter of which approximately corresponds to that of the membrane filter 5. As shown in FIG. 11, the spacer consists for example of a grid network of plastic material yarn and can be interposed between the membrane filter 5 of the sleeve 2A or 2B and the container 20 upon filtration (see FIG. 19).

Figure 12:
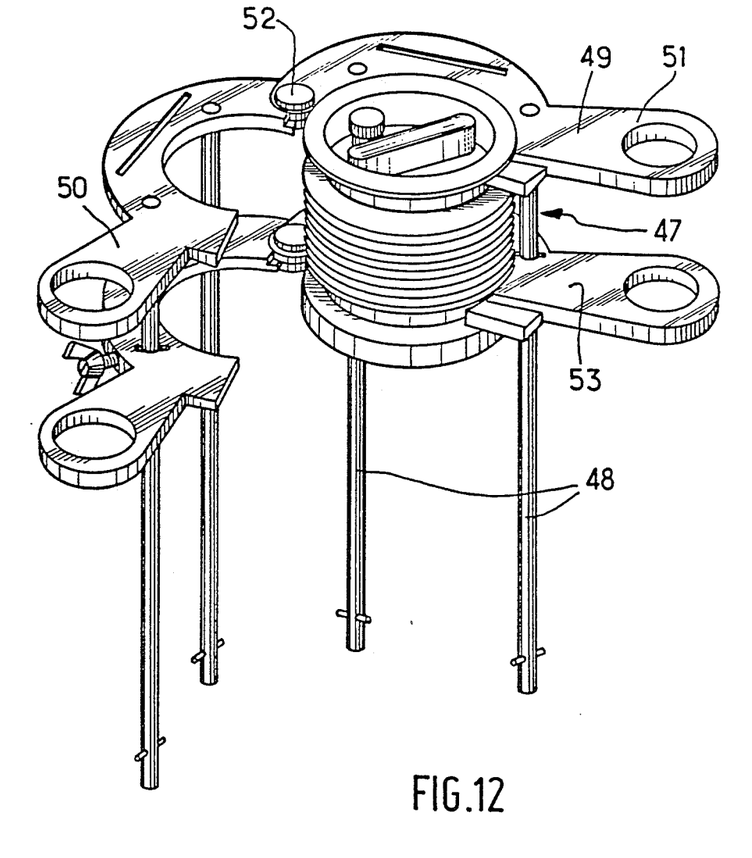
FIGS. 12 to 15 represent a holder in different positions containing a device according to the invention with a bellows sleeve showing both the container and cover.
Figure 15:
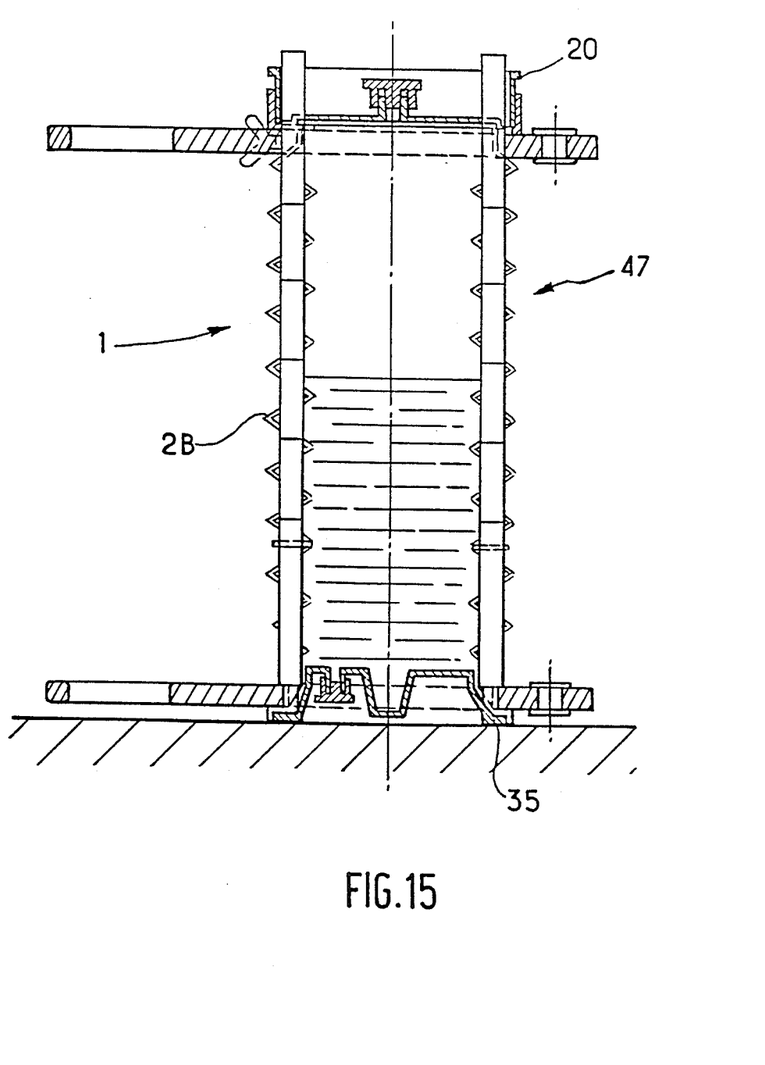

The device 1 having a bellows sleeve 2B can be placed if desired on a holder 47 such as shown in FIGS. 12 and 15 together with its container 20, cover 35, (which forms an assembled unit) and possibly the spacer 46. This holder 47 consists of four vertical feet 48 made integral with an upper collar 49 comprising two branches 50 and 51 similar to the branches of a pair of scissors and pivotable about a rotational axis 52. Each branch of the collar 49 is formed with a semi-circular slot which matches the substantially cylindrical portion 13 of the upper end 4 of the ringed sleeve. The holder 47 is also provided with a lower collar 53 identical to the upper collar 49 except for the fact that the feet 48, which are made integral with the collar 49, are slidable in both branches of the collar 53.

The process for conducting microbiological testing according to the invention will now be described by showing the operation of the device just discussed above as used in the testing of an aqueous solution to determine the number of microorganisms contained therein. It is important to note that the sample of liquid to be tested can be used with a device 1 either with a bellows or non-bellows sleeve (2B or 2A) to effect filtration of the sample through the membrane filter 5. For purposes of the following discussion, the device 1 in use includes a bellows sleeve 2B with many convolutions 7. For such a device, it is recommended to utilize the holder 47.

Figure 13:
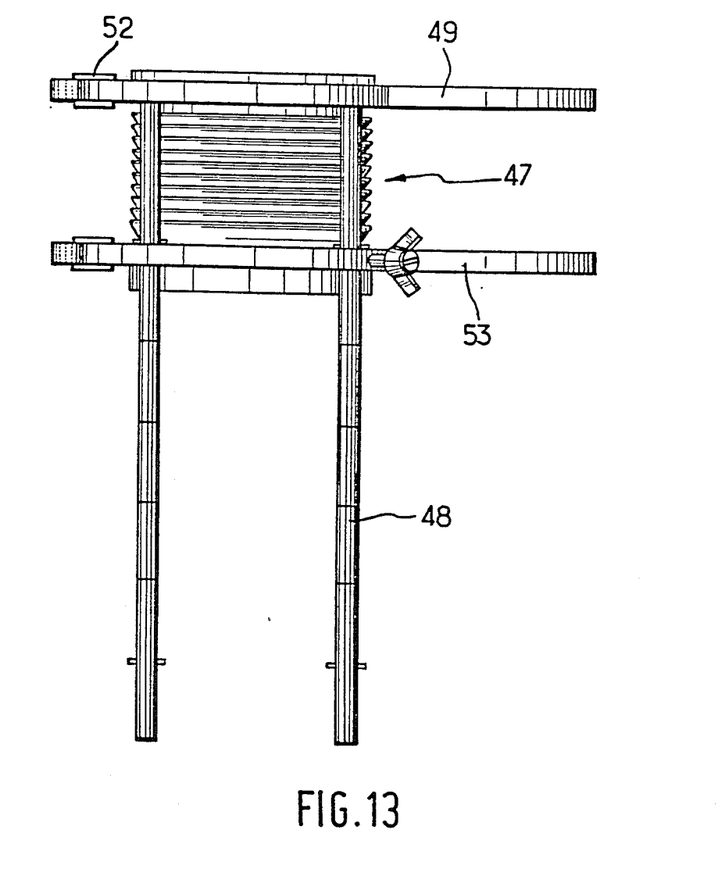
Figure 14:
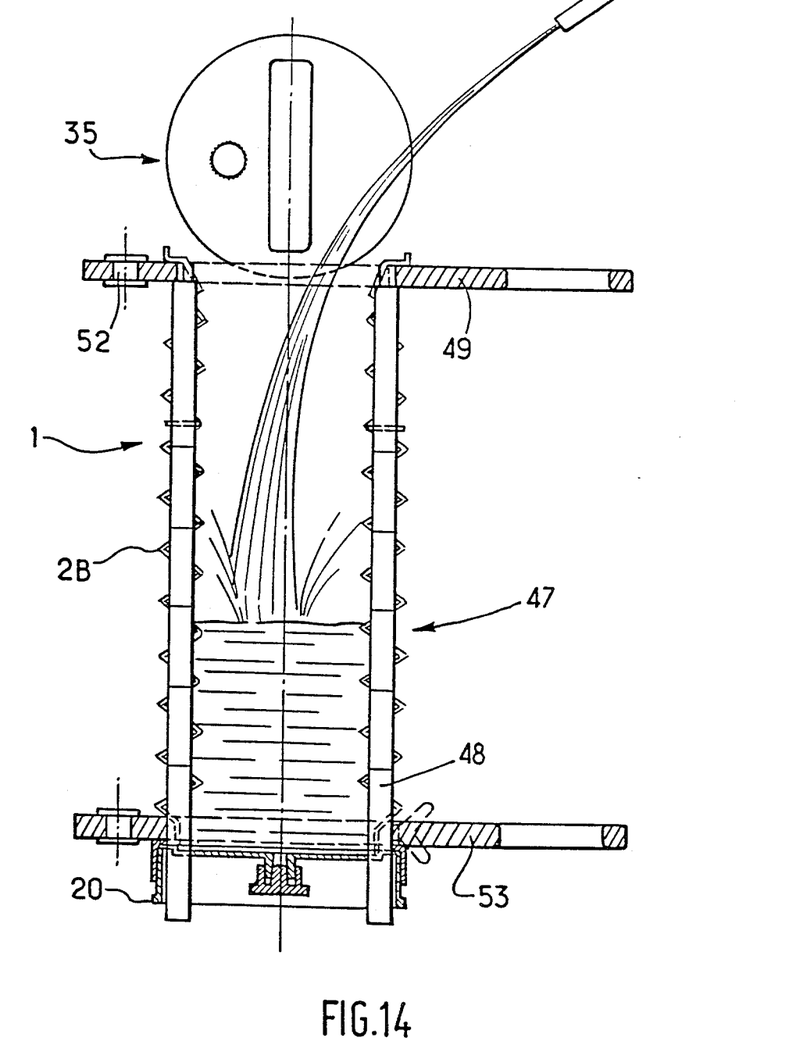

The assembled unit having been sterilized is inserted into the holder 47 by spreading the branches of the collars 49 and 43 apart and aligning the cylindrical portions 13 and 10 of the ends 4 and 3 with the semi-circular slots in one branch of the collars 49 and 53. Adjustments are made by setting the height of the lower movable collar 53 (FIG. 12). Closing the collars 49 and 53 results in the device 1 being firmly inserted into the holder 47 (See FIG. 13). To produce maximum extension of the bellows sleeve 2B, the movable collar 53 is slid away from the fixed collar 49. To introduce a sample of the liquid to be tested into the container having then a maximum volume either the cover 35 or its removable stopper 45 is removed (see FIG. 14).

After the sample is filled the device is tightly closed by the cover 35 and its stopper 45. This permits the device to be turned over and held in the storage position as shown in FIG. 15. To avoid problems associated with storage or transfer of the sample during which the microorganisms might start multiplying, it is also possible to immediately filter the sample thereby increasing the accuracy of the count of said microorganisms.

Figure 16:
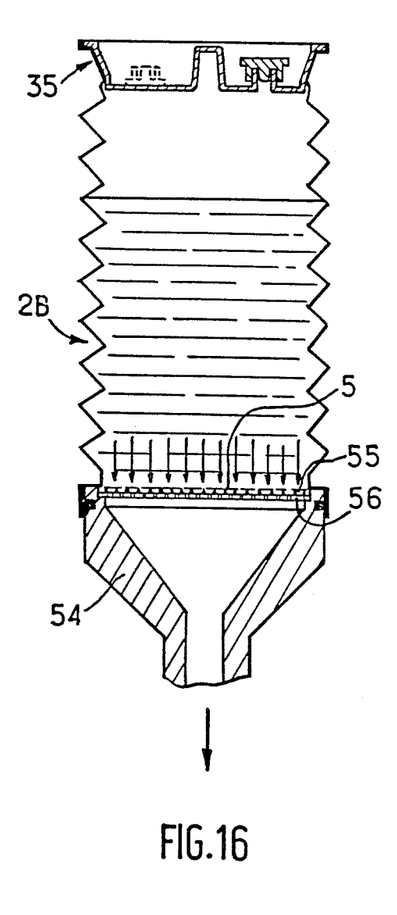
FIGS. 16 to 19 are sectional views of a device according to the invention as operated during filtration.
Figure 17:
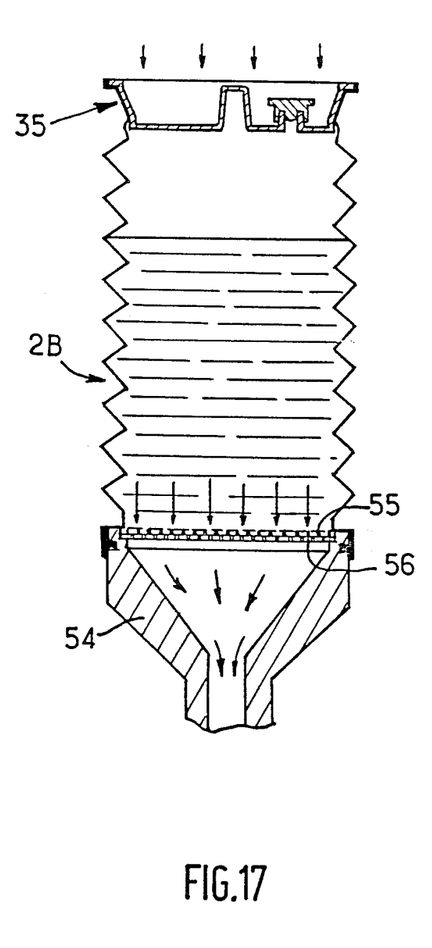
Figures 18, 19:
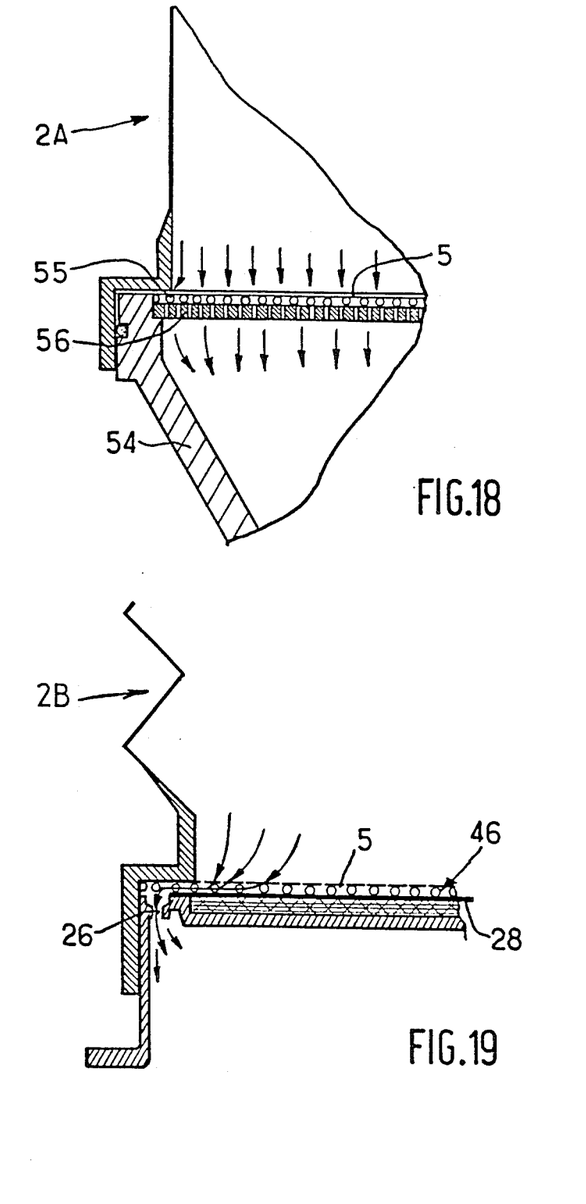

Filtration can be effected either with the use of a vacuum flask 54 in a known manner by placing the device with the container removed and the membrane end on the vacuum flask, and by evacuating the flask downstream of the membrane, or by pressing down on the device cover causing the bellows sleeve 2B to collapse to create pressure upstream of the membrane (see FIGS. 16, 17, and 18). In both of these instances, the membrane 5 rests on a spacer 55 disposed on a porous holder 56.

When filtration of the sample is to be achieved directly in the field where the sample is obtained in the absence of any laboratory materials such as a vacuum flask, the container 20 is used with the sealing element 28 covering the hollow portion 25 but not the peripheral zone containing the axial holes 26. Once again the assembled device 1 includes a bellows sleeve 2B which is manually pressed thereby causing the liquid to be tested to pass through the membrane filter 5 and the spacer 46 and thereafter out of the axial peripheral holes 26. In this manner the hollow portion which receives the culture medium is not wetted by the sample (see FIG. 19).

Figure 22:
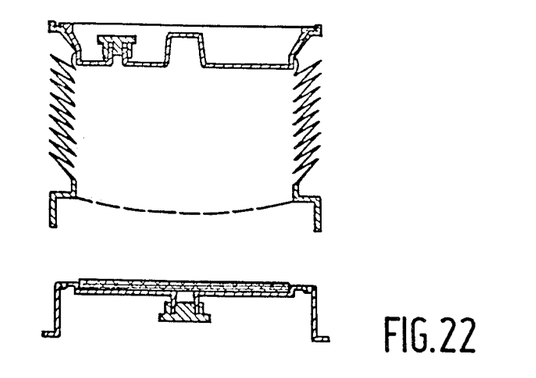
FIGS. 22 to 24 are sectional views of the membrane filter being brought into contact with a culture medium according to the invention.

Once filtration and, if desired, rinsing have been done, the wetted membrane filter 5 creates a barrier to gases. Thus the filter can be bulged as shown in FIG. 22 by slightly compressing the air contained in the sleeve 2B. This slight compression of the inside of the sleeve is easily accomplished by pushing the cylindrical portion 37 of the cover 35 into the corresponding cylindrical portion 13 of the end 4 of the sleeve.

The membrane filter is bulged without handling the membrane, and thus permits the user to check the integrity of the membrane on the one hand, while also permitting contact of the membrane with the culture medium from the membrane center to its periphery to avoid any entrapment of air bubbles which could impair the results of the test to be effected.

Figure 23:
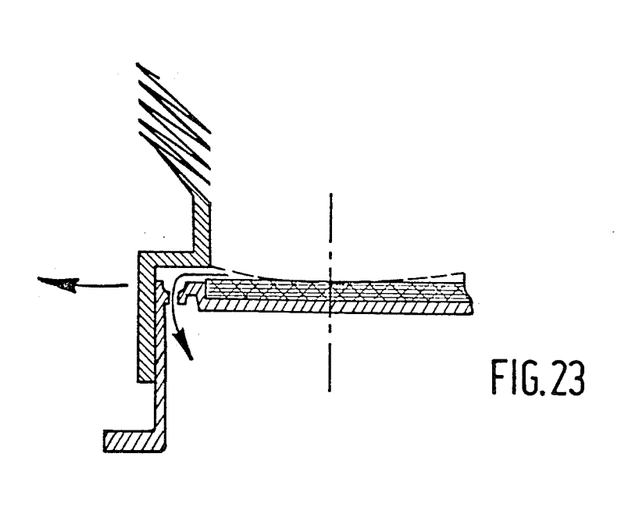
Figure 24:
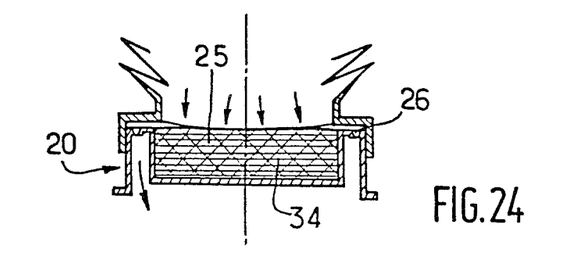

The contacting of the downstream side of the membrane filter 5 with the culture medium 31 or 34 is effected by forcibly nesting the container 20 after the sealing element 28 has been removed into the lower end of the device 1. Preferably the container has been prefilled with medium, otherwise it must be filled in situ. During nesting of the container the membrane filter 5, which has a bulging shape as explained previously, will be first contacted at its center by the upper face of the culture medium then progressively applied to the rest of the filter. Air is discharged at the periphery through the axial holes 26 of the container as shown in FIGS. 23 and 24. By appropriately selecting the plastic materials for the container and the sleeve 2A or 2B (i.e., a more rigid material is selected for the container than for the sleeve) complete nesting of the container into the end 3 of the sleeve produces tension in the membrane filter 5 to bring the ends thereof into contact with the planar upper face of the culture medium.

Thus, according to this invention, manipulation of the membrane filter 5 is achieved without touching the membrane and the culture medium is applied under optimum conditions so as to avoid any entrapment of air bubbles and undesired folds in the membrane.

Figure 25:
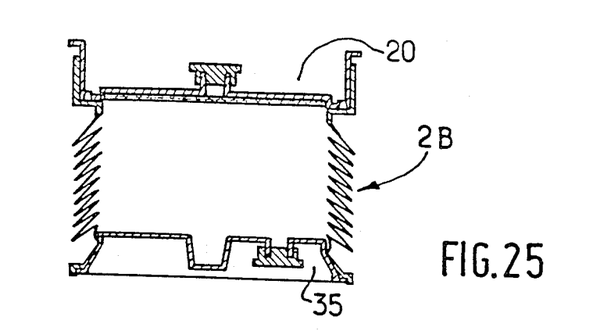
FIG. 25 is a sectional view of a bellows sleeve device according to the invention ready for incubation.
Figure 27:
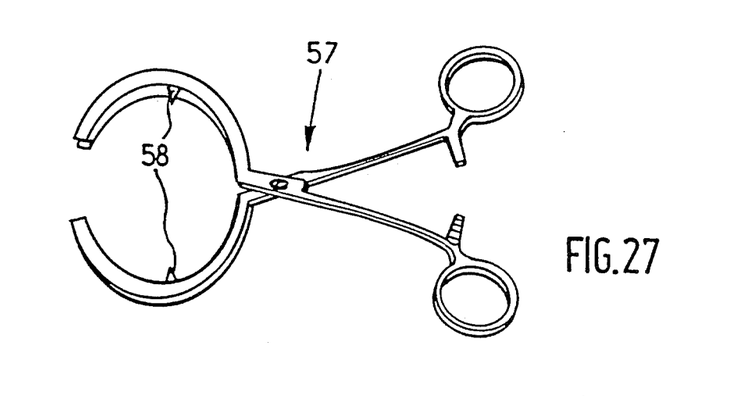
FIG. 27 shows the cutting pliers.

After depositing the culture medium on the lower face of the membrane filter 5 (i.e., the face opposite from that on which the microorganisms have been collected), the device can be directly incubated in an incubator, preferably by turning it over as shown in FIG. 25. However, if the volume of the device to be incubated must be limited in view of the available space in the incubator, the sleeve (whether bellows configuration or not) can be severed to reduce the height of the device. This is accomplished by a pair of cutting pliers 57 shown in FIG. 27 which are shaped like a pair of scissors with semi-circular arms that have a sharpened tooth 58 directed inwardly for perforating the sleeve when the pliers are closed on the circumference of the sleeve. Severing occurs by rotating the device with respect to the pliers. The height at which the sleeve is severed may be any level thereof, it being understood that before discarding the section of the sleeve which does not comprise the membrane, the cover 35 is retained for insertion on the severed section of the sleeve including the membrane 5.

Figure 26:
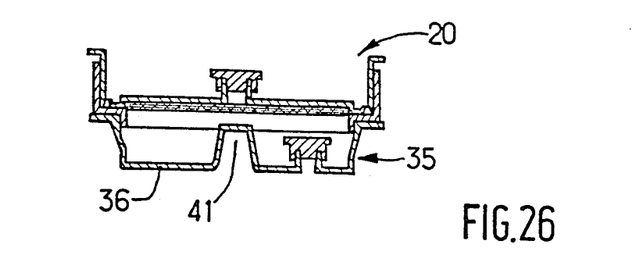
FIG. 26 is a sectional view of a device, either of the bellows or non-bellows configuration, severed by means of a pair of cutting pliers and ready for incubation.

For example, in case of a bellows sleeve 2B, severing can be achieved by leaving the last two convolutions 7 which connect to the end 3 of the sleeve so that the cover 35 can be put back without turning it over (i.e., in the direction shown in FIGS. 16, 17 22 or 25) upon the severed section of the sleeve. This height is such as to prevent the bottom 36 of the cover from coming into contact with the membrane filter 5. Preferably, the sleeve is severed on the cylindrical portion 10 of the end 3 a few millimeters above the membrane filter 5, and the severed section which includes the membrane and the container 20 is inserted into the inner cylindrical portion 40 of the cover 35 as shown in FIG. 26. The other severed section of the sleeve is removed and discarded. In this instance, the cover 35 is disposed with respect to the container 20 in a direction opposite to that of filtration. The device which includes the container 20, that portion of the end 3 comprising the membrane filter 5, and the cover 35 is then incubated, preferably with the cover facing downwardly and the container upwardly as shown in FIG. 26.

Figure 29:
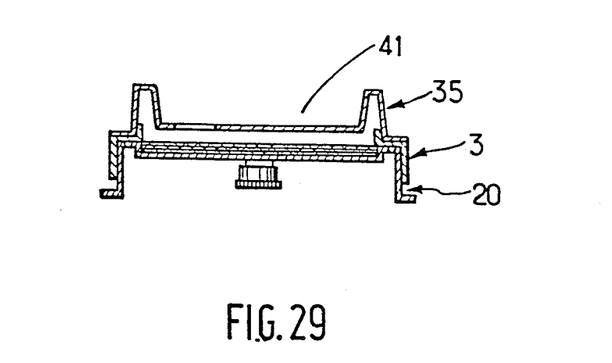

After incubation is completed, the colonies of microorganisms which developed at the surface of the filtering membrane 5 must be counted. This is accomplished by severing the sleeve (if this was not previously done) along its cylindrical portion 10 with the section containing the membrane being applied to the inner cylindrical portion 40 of the cover 35 to create the device shown in FIGS. 26, 28, 29. Colony reading occurs with this device being disposed so that the container 20 faces downwardly and the end 3 with its membrane filter 5 clamped between the container 20 and the cover 35 facing upwardly (see FIGS. 28 and 29).

If the nature of the microorganisms inspected for permit, and if the number thereof is small, one can read the number of colonies developed on the membrane 5 by withdrawing the cover 35 from the end 3. If this is not the case, or if it is preferred to leave the cover 35 in its position, the hollow portion 41 of the cover 35 being much closer to the membrane filter 5 than the remainder of the surface of the circular bottom 36 of the cover allows the reading of the number of colonies to be made through the bottom of the hollow portion without the observer being hampered by condensation, which usually occurs on those portions of the bottom 36 most remote from the membrane, i.e., not on the hollow portion 41.

Counting colonies in this manner allows the use of unmarked (i.e., unsquared) membranes thereby facilitating membrane rinsing operations, increasing the filtration area and reducing membrane costs. Also, as soon as the device is removed from the incubator, the thermal contrast between the incubation temperature and the ambient temperature causes rapid condensation on the circular bottom 36 of the cover, except on those surfaces which are remote therefrom, in particular the hollow portion 41, through which the reading of the number of colonies of microorganisms to be evaluated is made.

To facilitate colony reading, the hollow portion 41 can be given a convex shape to form a magnifying glass, and moreover, the largest portion of the hollow portion 41 can be made opaque as shown in FIGS. 10 and 28 so as to leave only an observation window 42. A full 360° rotation of this observation window 42 over the membrane filter 5 produces the circular zone 43 corresponding to a determined percentage of the surface of the membrane, for example 50%, and on which the number of visible colonies can be counted.

Thus, the present invention provides a disposable microbiological testing device which may be packaged in a small volume, but may, however collect a sample of much larger volume (e.g., the volume of a bellows sleeve can vary between 80 and 320 $cm^3$), is directly usable in the field to collect and filter the liquid sample to be tested, does not retain bacteriostatic agents, allows the user to verify membrane integrity after filtration, ensures application of the membrane filter upon the culture medium without folds and air bubbles, and finally permits easy reading of the number of microorganisms to be counted after incubation.

It is to be understood that the foregoing is solely illustrative of the invention which is to be limited only by the claims defined below.

I claim:

1. A device for microbiological testing of a liquid sample by means of a membrane filter comprising:
   a sleeve having a first end and a second end;
   a membrane filter fixed at its periphery to said first end of said sleeve;
   each of the ends of said sleeve being formed as a female receptacle;
   a container shaped to be matingly inserted into said first end and to support said membrane when matingly inserted;
   said container comprising a hollow section having a bottom surface and a peripheral wall surrounding said bottom surface, an absorbent material positioned within said hollow section and a removable sealing element sealed to said peripheral wall to prevent liquid from passing through said sealing element;
   said container having holes providing a communication path from the sleeve to the space under the container, and wherein said sealing element is located in such a way as to not cover said holes;
   said container for housing a culture medium in said absorbent material for application thereof under said membrane filter;
   said second end of said sleeve shaped to receive a cover for ensuring substantial closing of said device.

2. A device according to claim 1 wherein said sleeve is a bellows having compressible, expandable convolutions to permit said sleeve to define an inner minimum volume when all the convolutions are compressed and an inner maximum volume when all the convolutions are expanded.

3. A device according to claim 2 wherein said convolutions have a triangular cross-section defined by two unequal sides which form different acute angles with the axis of the sleeve, the larger side of the convolution connecting said first end of the sleeve where the membrane filter is fixed.

4. A device according to claims 1, 2 or 3, wherein said first end adjacent the membrane filter comprises a first substantially cylindrical portion connected to said sleeve, said cylindrical portion including a circular edge portion extending radially outwardly in a plane substantially perpendicular to the axis of the sleeve and forming an angle with said first cylindrical portion, and a second cylindrical portion connected to said circular edge portion.

5. A device according to claims 1, or 3 wherein the female receptacle at the second end of said sleeve comprises a conically tapered portion and a collar extending from said tapered portion.

* * * * *